(12) United States Patent
Parker et al.

(10) Patent No.: US 6,756,789 B1
(45) Date of Patent: Jun. 29, 2004

(54) METHOD FOR IMAGING LOGS OR STEMS AND APPARATUS

(75) Inventors: Richard Parker, Rotorua (NZ); Christine Todoroki, Rotorua (NZ)

(73) Assignee: New Zealand Forest Research Institute Limited (NZ)

( * ) Notice: Subject to any disclaimer, the term of this patent is extended or adjusted under 35 U.S.C. 154(b) by 0 days.

(21) Appl. No.: 09/979,993

(22) PCT Filed: May 29, 2000

(86) PCT No.: PCT/NZ00/00084
§ 371 (c)(1),
(2), (4) Date: Mar. 15, 2002

(87) PCT Pub. No.: WO00/72652
PCT Pub. Date: Dec. 7, 2000

(30) Foreign Application Priority Data

May 27, 1999 (NZ) ................................. 335988

(51) Int. Cl.[7] .......................... G01R 27/04; G01R 27/32
(52) U.S. Cl. ........................................ 324/637; 324/644
(58) Field of Search ................................ 324/637, 638, 324/639, 642, 644; 144/364, 357; 209/518, 576

(56) References Cited

U.S. PATENT DOCUMENTS

| | | | |
|---|---|---|---|
| 4,123,702 A | | 10/1978 | Kinanen et al. |
| 4,185,672 A | * | 1/1980 | Vit et al. ................. 144/357 |
| 4,500,835 A | | 2/1985 | Heikkila |
| 4,607,212 A | * | 8/1986 | Jakkula ..................... 324/637 |
| 5,128,621 A | * | 7/1992 | Berthaud et al. ........... 324/639 |
| 5,593,530 A | * | 1/1997 | Hashiguchi ................. 156/260 |
| 5,892,808 A | | 4/1999 | Goulding et al. |

FOREIGN PATENT DOCUMENTS

| | | |
|---|---|---|
| GB | 1489554 | 10/1977 |
| GB | 1564194 | 4/1980 |
| WO | WO 9709611 | 3/1997 |

* cited by examiner

Primary Examiner—Albert Decady
Assistant Examiner—James Kerveros
(74) Attorney, Agent, or Firm—Dann, Dorfman, Herrell and Skillman, P.C.

(57) ABSTRACT

A method and apparatus for assessing standing tree stems for readiness for harvesting, or for determining cutting points for processing of felled tree stems, logs, or wood pieces, or for assessing stems, logs, or wood pieces for a particular end use, includes scanning with short-wave or microwave electromagnetic energy and processing the scan data to produce an image indicating the external shape or dimensions of the stem or log and hidden internal characteristics and their position, and assessing the image. Knots and/or whorls, which are not visible from the exterior and the depth of the clear wood sheath from the surface, may be determined.

30 Claims, 11 Drawing Sheets

Large end of log

METHOD FOR IMAGING LOGS OR STEMS AND APPARATUS

FIELD OF INVENTION

The invention comprises a method and apparatus for imaging both external and internal characteristics of standing tree stems, or felled stems logs, or wood pieces including hidden internal features such as the presence and position of knots or whorls which are not necessarily externally visible, resin pockets, internal checks, annual growth rings, sapwood and heartwood or sapwood-heartwood transitions, earlywood and latewood, and the depth of the clearwood sheath in a pruned stem or logs or from a pruned stem.

BACKGROUND

In New Zealand commercially grown *Pinus radiata* are often pruned of branches at a number of intervals over the 25 to 30 year typical growth period between planting and harvesting. This is also the case for southern pine species in the USA. Such pruning may result in a defect core, including knots, becoming hidden within the tree stem as a tree continues to grow and subsequent growth rings cover the branch stub end, or more commonly where a number of branches have been pruned at the same height on the stem a whorl of knots remains within the tree stem, which again may commonly become hidden as the tree continues to grow. Knots or whorls and other internal characteristics such as resin pockets or internal checks (voids) are considered defects within the wood. They typically render the wood unsuitable for higher value wood applications and are structural weaknesses such that timber pieces including such defects may be unsuitable for structural applications. The zone of wood formed outside the defect core is known as the clearwood sheath and typically contains high value, defect free wood. The presence of such hidden internal defects and the volume of clearwood is general not known until after the logs have been sawn, when the presence of internal defects is revealed. There are currently no known practical, accurate and reliable methods for predicting in detail the quality and potential value of the wood within mature standing tree stems especially pruned stems. The currently most accurate prediction methods require felling a sample of the mature trees and either destructively analysing the sample in the forest, or processing them and intensively studying the resulting products.

In general tree stems are assessed by visual assessment and measurement of externally visible characteristics by skilled workers as to the apparent optimum cutting points for bucking the tree stems into logs. Similarly, stems or logs are commonly visually assessed for suitability of the wood for a particular end use, such as structural or other solid wood applications, veneer production, or pulp and paper production.

There are a number of patents in the prior art which disclose the scanning of sawn timber with radar or microwave frequency radiation in systems for detecting the presence of knots on the surface of the sawn timber, such as U.S. Pat. Nos. 4,607,212, 4,500,835, and 4,123,702, and UK patent 1,489,554 for example.

SUMMARY OF INVENTION

In broad terms in one aspect the invention comprises a method for assessing standing tree stems, or for determining cutting points for processing of felled tree stems, logs or other wood pieces, or for assessing stems, logs, or wood pieces for end use, comprising scanning a stem, log or piece with shortwave or microwave electromagnetic energy, detecting the energy reflected from the wood, processing the resulting scan data to produce an image indicating hidden internal characteristics and their position within the stem, log, or piece, and assessing the image together with information to the external shape or dimensions of the stem, log, or piece and identifying cutting points for the stem, log, or piece or allocating the stem, log, or piece or part of parts thereof to an end use.

Preferably information as to the external shape and dimensions of the stem, log, or piece and the depth of detected internal characteristics is all obtained from the scan data.

Preferably the method includes determining the depth of the clearwood sheath from the surface of the wood for a pruned stem.

In broad terms in another aspect the invention comprises apparatus for assessing standing tree stems, or for determining cutting points for processing of felled tree stems, logs or other wood pieces, or for assessing stems, logs, or wood pieces for end use, comprising scanning means arranged to scan the stems, logs, or pieces with shortwave or microwave electromagnetic energy and to detect the energy reflected from the wood, associated computer processing means arranged to process the resulting scan data as to internal characteristics of the stem, log, or piece together with information as to the external shape or dimensions of the stem, log, or piece and produce an image of both the external shape and indicating hidden internal characteristics and their position and the depth of clear wood within each stem, log, or piece.

The electromagnetic energy may be radar frequency energy or microwave frequency energy. A preferred frequency is in the range 0.5 to 20 GHz, more preferably 5 to 10 GHz, and most preferably about 8 GHz.

The method and apparatus of the invention are directed to both the detection of hidden defects such as knots or whorls or other defects within the stems, logs or wood pieces, which are not readily visually apparent from the exterior. This may be by assessment of stems of standing trees before felling to determine their readiness for harvesting, or by assessment of felled stems before bucking into logs or before sawing of logs into timber pieces in a sawmill or peeling of bolts in a veneer plant, to obtain the optimum cutting points. The cutting point or end use may be determined taking into account the depth of clearwood and presence of hidden defects, and to maximise the economic value obtained from the harvested trees. In addition the invention involves producing an image showing the internal hidden characteristics and preferably in addition the external shape of the stem or log or wood piece, and assessing the image to identify the optimum cutting points for or to allocate the stem, log or wood piece or parts of it to a particular end use such as sending of the log to a sawmill for processing to structural or finishing grade timber or to a veneer plant, or sending of the log for chipping for pulp and paper production for example. Preferably the external shape and dimensions of the stem or log or wood piece are obtained from the scanned data but alternatively information as to the external shape and/or dimensions of the stem or log or wood piece may be obtained by other means such as an electronic measuring device or system or a scanning system using another technology. The resulting image of the stem or log may be displayed to and assessed by an operator on a screen, or alternatively may be an image in electronic form which is further processed by software to identify the optimum cutting points or optimum end use for the stem or log or parts thereof with the resulting information being displayed to an operator, printed on a tag which is attached to the stem or log comprising information as to optimum cutting points or end use, or passed to the control system of a further online processing stage involving automated cutting of stems into logs or logs into timber pieces, or allocation or redirection of logs for solid wood or pulp and paper end use.

BRIEF DESCRIPTION OF THE FIGURES

The invention is further described with reference to the accompanying figures in which.

DETAILED DESCRIPTION OF PREFERRED FORMS

Figure 1:
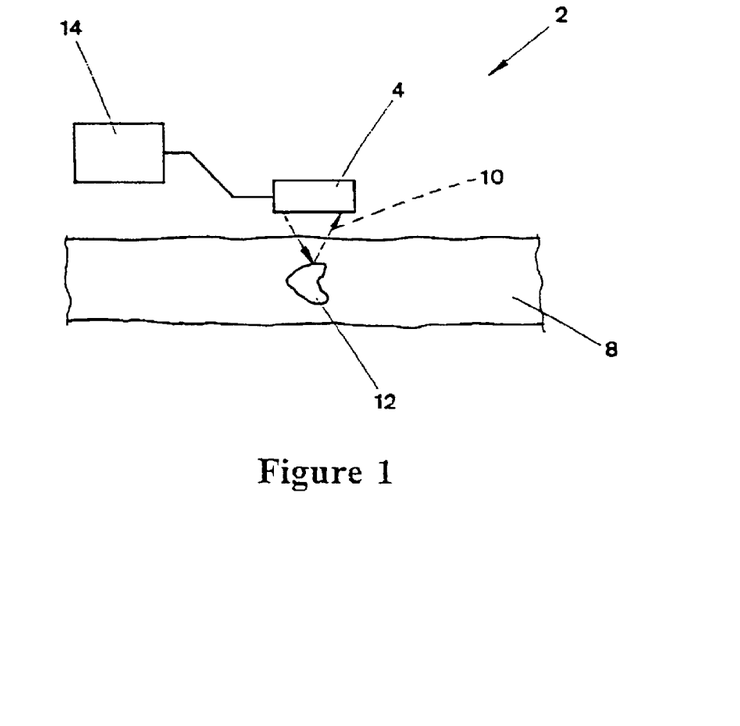
FIG. 1 is a schematic diagram of one scanner configuration for assessing tree stems, logs, or wood pieces.

FIG. 1 shows scanning apparatus 2 arranged to operate on either standing trees or felled stems, or logs. The apparatus comprises one antenna and receiver 4 arranged to direct short wave electromagnetic energy towards the stem or log 8 and to detect reflected energy. Preferably the short wave electromagnetic energy is in the range of 0.5 GHz to 20 GHz, more preferably about 5 to 10 GHz, and most preferably about 8 GHz, although radar or microwave energy outside this band may be used. Air launched scanning may provide a profile of the external stem or log shape and dimensions. The beam is caused to scan the log or stem. The antenna 4 may be moved along the long axis of a stationary felled stem or log, or may be moved up and down a standing tree. Alternatively a felled stem or log may be moved by a conveyor relative to a stationary antenna.

The antenna 4 detects the differences in dielectric properties between different regions of the wood. The strength or clarity of the reflection is greatly determined by the level of dielectric contrast between the changing dielectric interface (material change boundaries). The main influence on dielectric property changes is water/moisture. Identical materials with different water contents will have different dielectric properties. Air has a dielectric constant of 1 and water has a dielectric constant of 81. Fresh radiata pine has a dielectric of approximately 65. Different parts of the stem have differing dielectric properties due to internal characteristics in the wood (eg growth rings, heartwood/sapwood, knots) and their location in relation to the stem surface. A hidden internal feature, shown as a whorl, is indicated at 12. Other internal characteristics which are detected may be for example, defect core, juvenile wood, wandering pith, compression wood, resin pockets, internal checking and possibly spiral grain.

Figure 2:
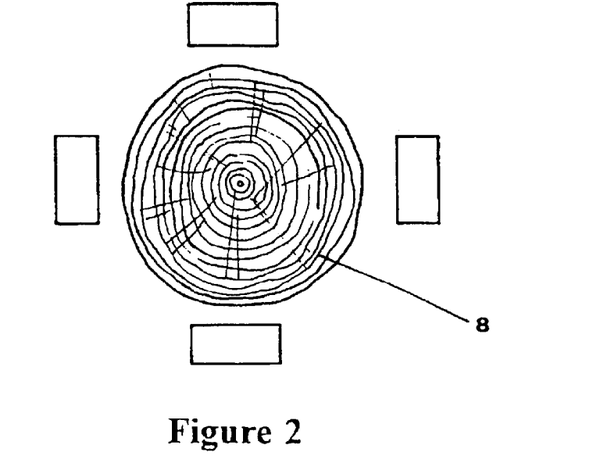
FIG. 2 is a schematic diagram of another scanner configuration.

In a preferred form the apparatus comprises a number of antennae spaced around the log or stem which scan the log or stem from more than one direction. FIG. 2 shows four antennae positioned around the circumference of log 8. For example one antenna may be positioned below a conveyor by which logs or stems are carried past the scanner, and one or more other antennae may be positioned above and/or to the sides of the conveyor.

Figure 3:
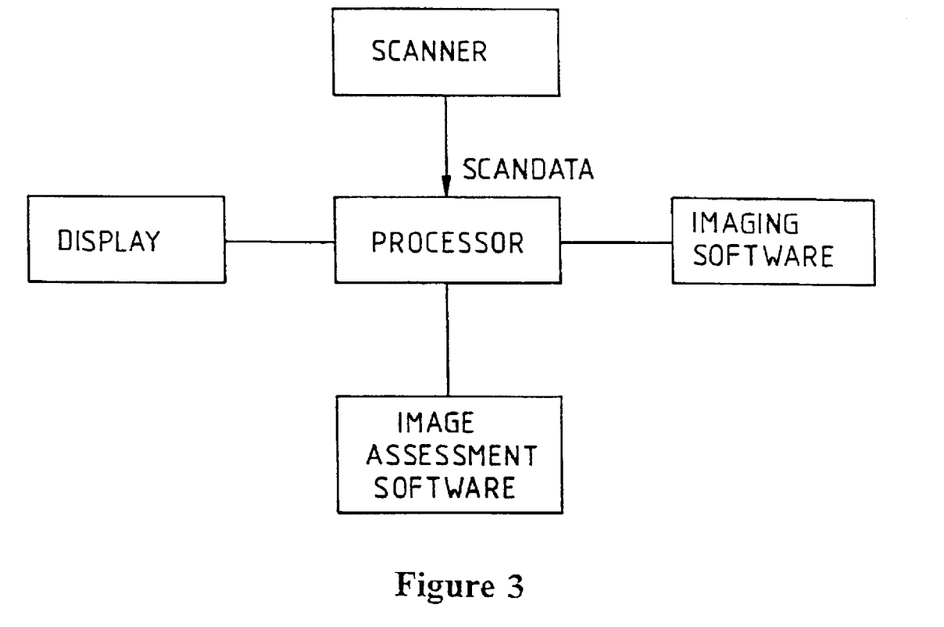
FIG. 3 is a block diagram of apparatus of the invention.

Referring to FIG. 3 the raw data resulting from scanning is passed to a computer processor loaded with imaging software which processes the data and produces and displays an image of the stem, log, or wood piece, showing both the external profile and detected internal characteristics of the stem, log, or piece. The image may be displayed to and assessed by an operator on a screen. Alternatively the system may include software capable of determining an optimum bucking solution for the stem such as the IFR Logger available from IFR Technologies Ltd, New Zealand under the trade mark INVADER. Alternatively software capable of determining an optimum sawing pattern for the log such as that available from New Zealand Forest Research Ltd under the trade mark AUTOSAW may be arranged to assess the image and identify optimum cutting points for sawing the log. The cutting points may be displayed on the image or alternatively information of the cutting points may be passed to the control system of a further online automated sawmill.

The apparatus may be arranged to scan each log or stem in a single pass or in multiple passes. For example a conveyor may be arranged to carry each log forwards past a single or multiple antenna scanning stage, and then reverse the direction of travel of the log once the whole log has been scanned in the forward direction, after first rotating the log, to scan the log while travelling in the return direction. Optionally the log or stem may then move forwards again after being rotated through a further angle, to continue along the conveyor, three scans at different angles from the one or more antenna then having been taken. Some internal features may not show up on a single scan. A feature may be angled so that energy reflected from its surface is deflected away from and not received by the antenna at one angle.

Scanning in more than one direction or changing the orientation of the antenna may assist in detecting internal features.

Figure 4:
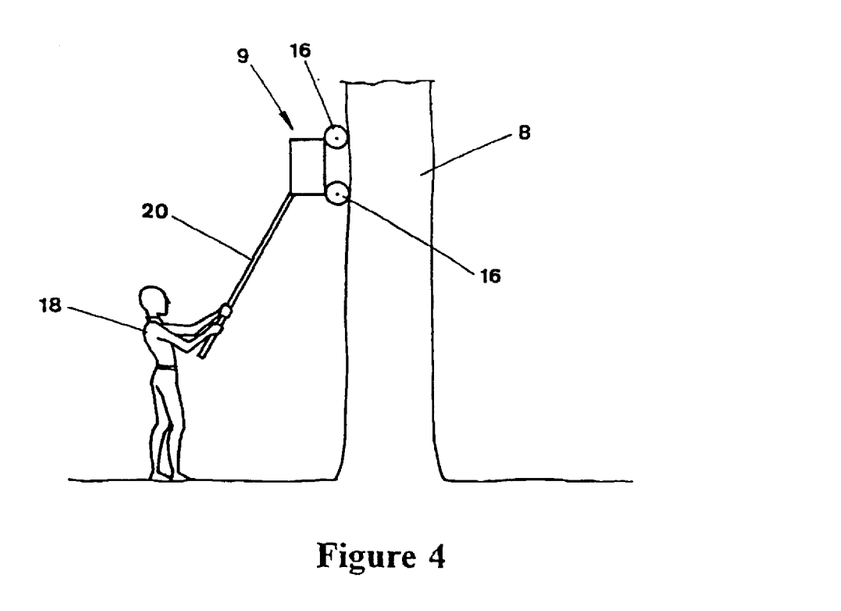
FIG. 4 is a schematic diagram of another scanner configuration for use on standing trees.

FIG. 4 schematically illustrates one configuration of apparatus 9 for use on a standing tree 8. The scanner is mounted on rollers 16 and is controlled by an operator 18 using a boom 20. The operator 18 places the rollers 16 against the tree and pushes the apparatus 2 up and down the tree using the boom 20. It is appreciated that the boom may be telescoped to assist the operator.

Figure 5:
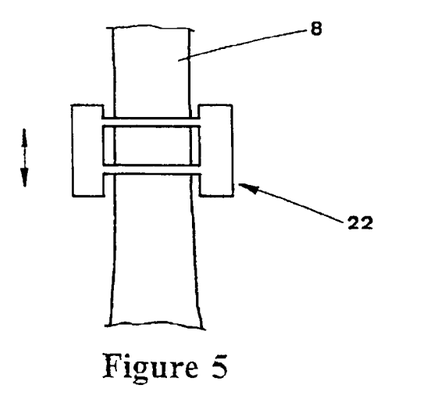
FIG. 5 is a schematic diagram of another scanner configuration for use on standing trees.

FIG. 5 illustrates another configuration of apparatus 22 for use on a standing tree 8. An autonomous mechanised and perhaps robotic tree climber 22 is arranged to travel up and down the tree. The apparatus may be formed as two sections hinged together which clip around and engage the trunk of tree. A drive system may be arranged to drive the apparatus up the tree stem until either a predetermined height has been reached or a branch is encountered.

Figure 6:
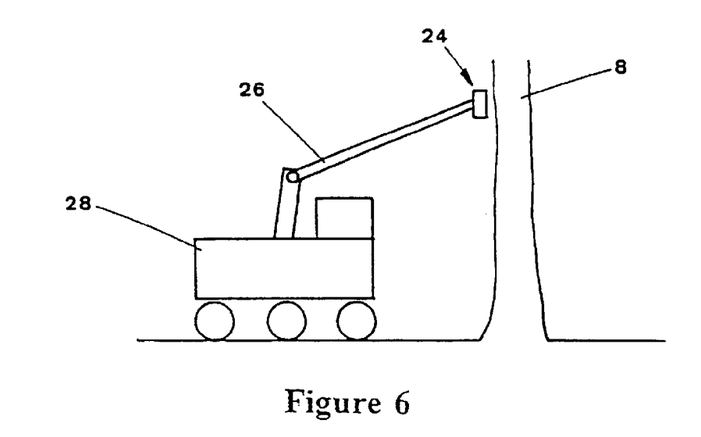
FIG. 6 is a schematic diagram of another scanner configuration for use on standing trees.

FIG. 6 shows scanner 24 mounted on a boom 26 and operated by machine 28 which controls the boom to move the scanner 24 up and down the trunk of the tree 8.

Such scanners of the invention may be used at the time of pre-harvest assessment to assist in planning decisions regarding the timing of harvesting and matching the wood resource with markets, as well as assisting in optimisation of processing decisions. For example, the amount of defect-free wood in a standing tree may be determined before harvesting. If the amount of clearwood is insufficient the tree may be left for harvesting at a later time or allocated to a different market or process.

Figure 7:
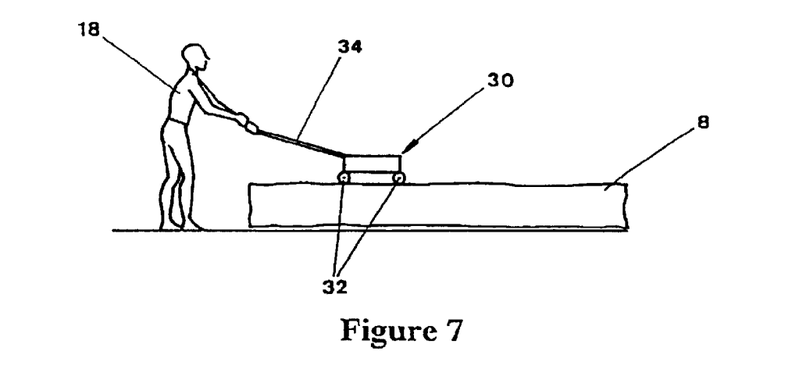
FIG. 7 is a schematic diagram of another scanner configuration for use on felled stems or logs.

FIG. 7 illustrates scanner 30 on rollers 32. The operator 18 places the rollers 32 on the surface of felled stem or log 8 and moves the scanner along the stem or log by handle 34. Alternatively the apparatus may be hand held by the operator.

Figure 8:
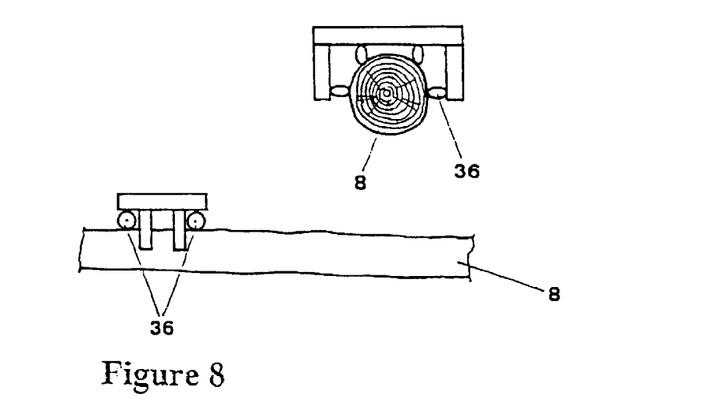
FIG. 8 is a schematic diagram of another scanner configuration for use on felled stems or logs.
Figure 9:
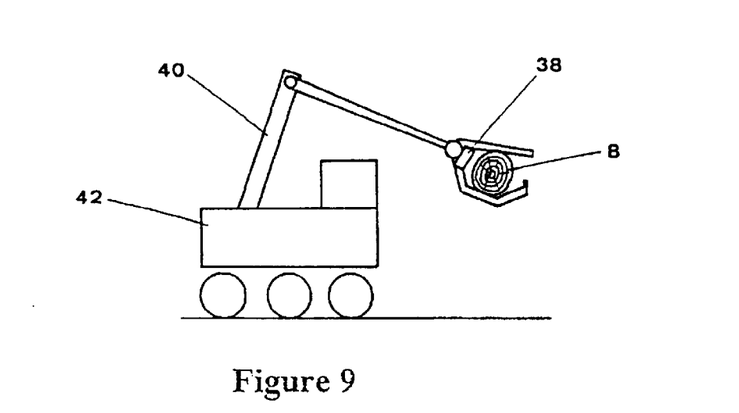
FIG. 9 is a schematic diagram of another scanner configuration for use on felled stems or logs.

FIG. 8 illustrates a scanner 34 which is arranged to travel along the stem or log 8 on rollers 36 as an autonomous robot.

Figure 10:
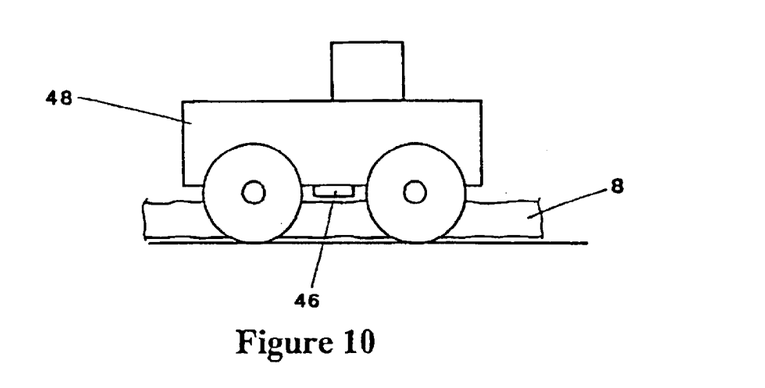
FIG. 10 is a schematic diagram of another scanner configuration for use on felled stems or logs.

FIG. 8 shows scanner 38 may boom mounted on a grapple 40 and controlled by machine 42. The machine 42 operates boom 40 so that the scanner 38 travels along the stem or log whilst held by the grapple. FIG. 10 shows scanner 46 mounted on machine 48 having wheels arranged to straddle and move along stem or log 8 on the ground.

Figure 11:
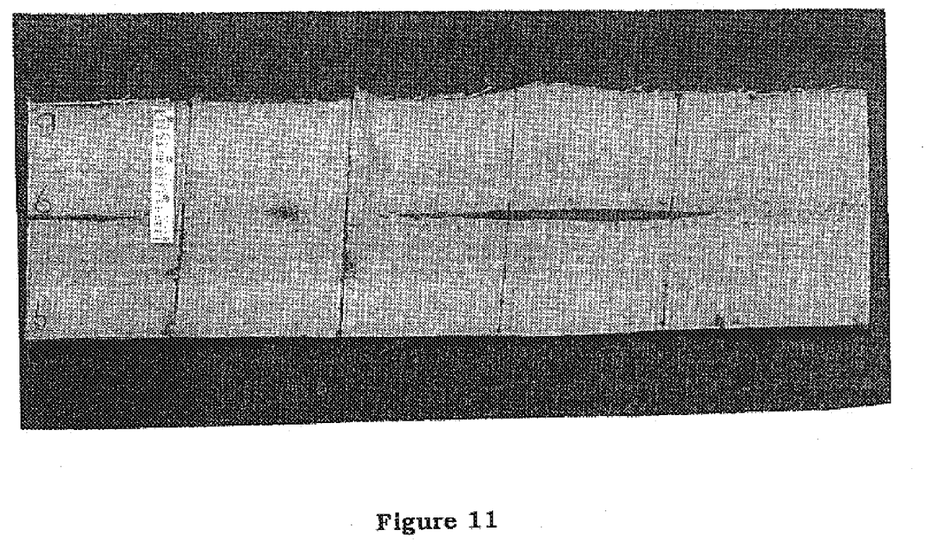
FIG. 11 is a photograph of a cut face of a section of a log which has been cut longitudinally.
Figure 12:
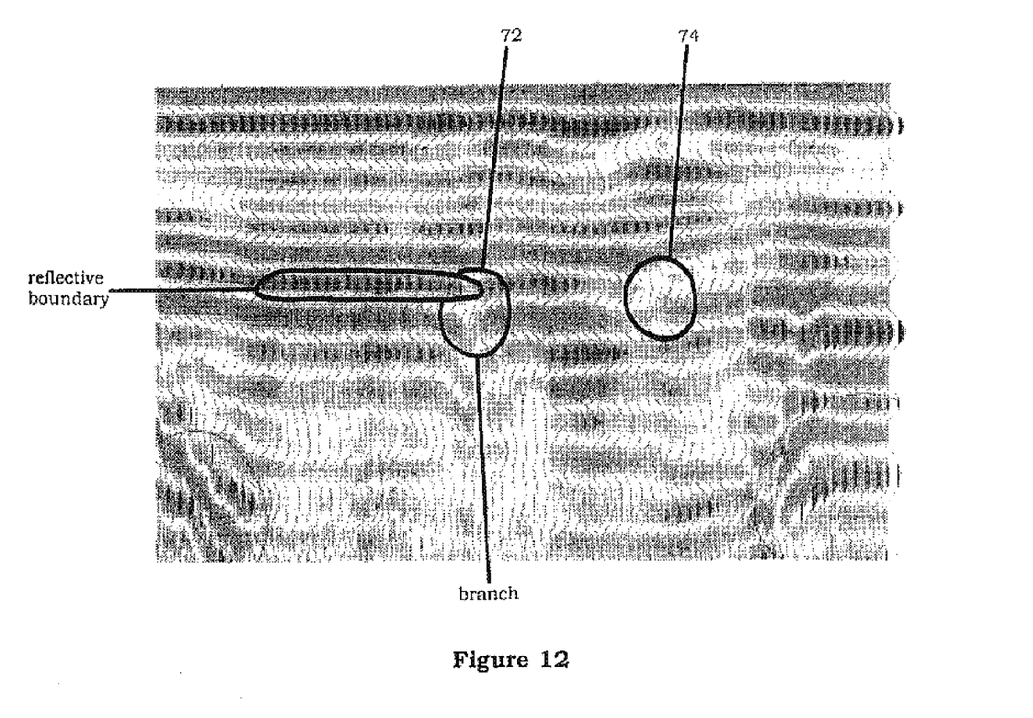
FIG. 12 is an image of the log section of FIG. 11, produced by the method of the invention before the log was cut.

FIG. 11 is a photograph of the cut face of a section of log which has been cut longitudinally. FIG. 12 shows an image of the section of the log produced by scanning according to the method of the invention before the log was cut.

Figure 13:
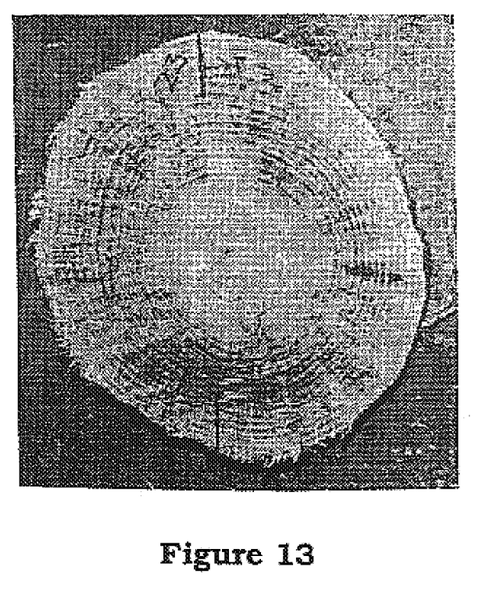
FIGS. 13 and 14 are photographs of cut faces of another log 1.3 and 2.7 meters from the large end of the log.
Figure 14:
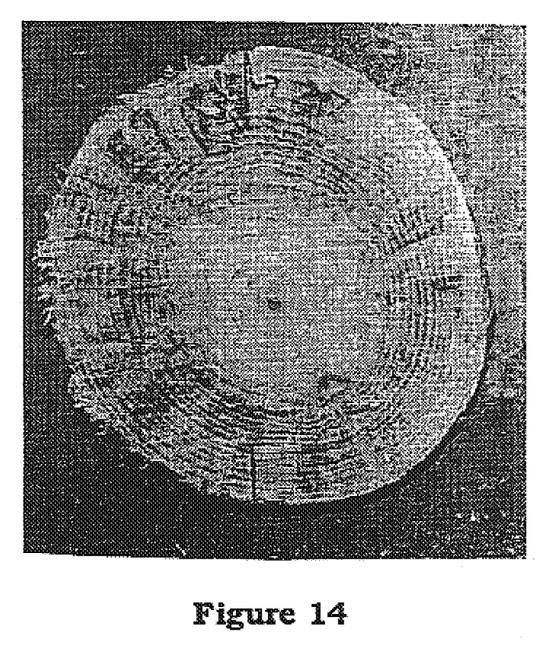
Figure 15A:
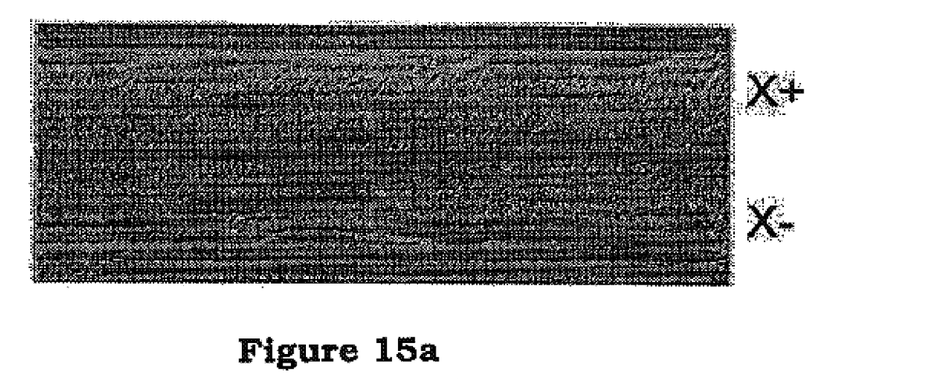
FIGS. 15a and 15b are X and Y axis images of the log of FIGS. 13 and 14 taken before the log was cut.
Figure 15B:
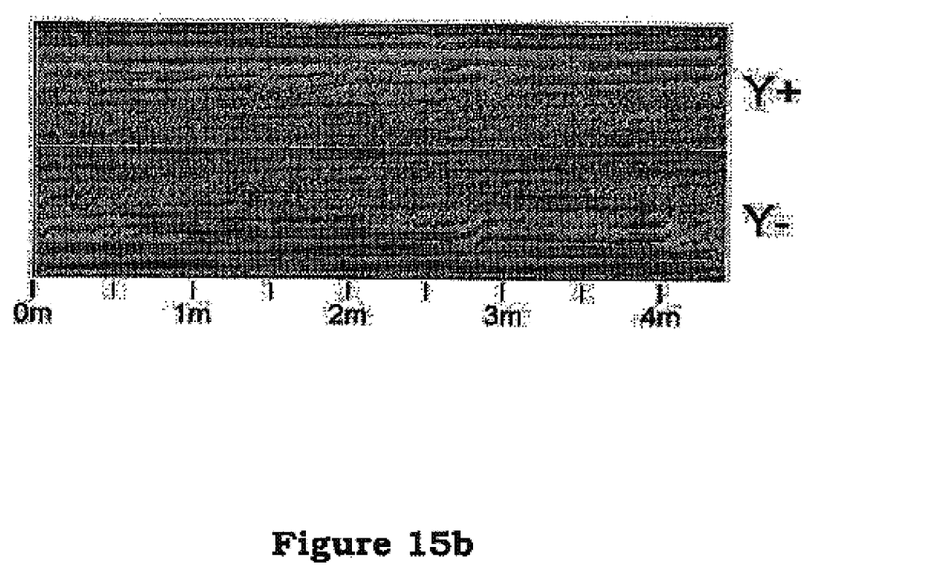
Figure 16:
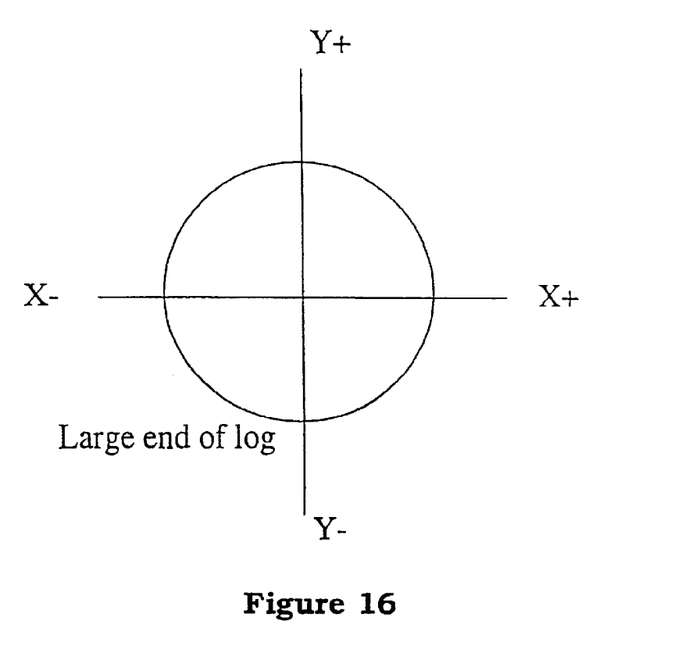
FIG. 16 shows the arrangement of the X and Y axes of the log.

FIG. 13 is a photograph of a cross-sectional cut of a log showing occluded branches 1.3 m from the large end of the log. FIG. 14 is a photograph of a cross-sectional cut of the same log showing occluded branches 2.7 m from the large end of the log. FIG. 15 is an image produced by scanning the log with radar frequency radiation and detecting reflected radiation, of the X and Y axes of the log as shown in FIG. 16. FIG. 15 shows the location of the occluded branches and the clearwood zone above them.

Figure 17A:
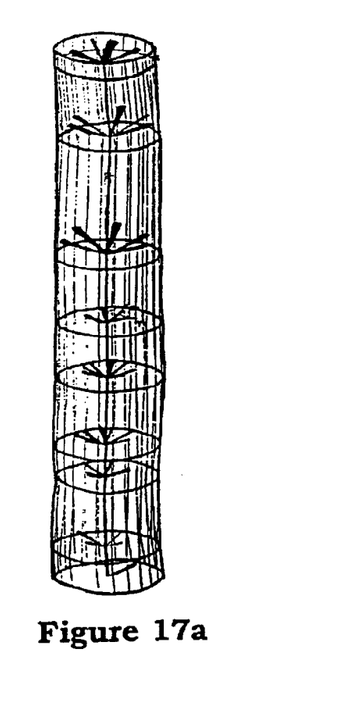
FIG. 17a pictorially illustrates a log and the location of whorls within the log as determined by sawing the log into discs, and FIG. 17b pictorially illustrates the same log showing whorls as determined by scanning according to the method of the invention.
Figure 17B:
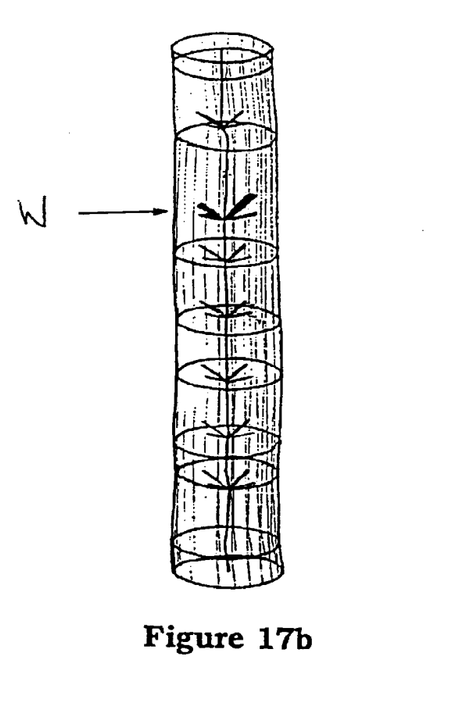
Figure 18:
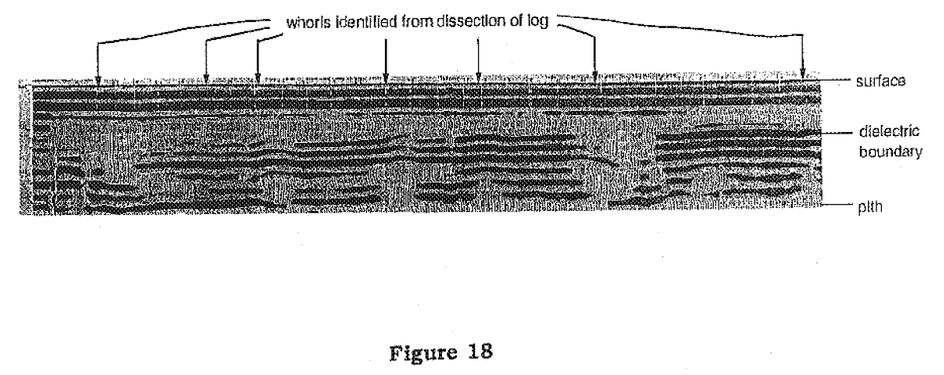
FIG. 18 is an image of the log of FIG. 17 produced by the method of the invention before the log was cut.

FIGS. 17a and 17b show the comparison between the actual location of branch whorls in a log as determined by cross-sectional analysis (by cutting the log into a series of disks)—FIG. 17a, and the estimated location of branch whorls from radar scanning—FIG. 17b. Radar scanning located an extra whorl which was fully within a cut disk and so not seen visually. FIG. 18 is a radar scan of the log showing the estimated location of whorls and the clear wood zone.

Figure 19A:
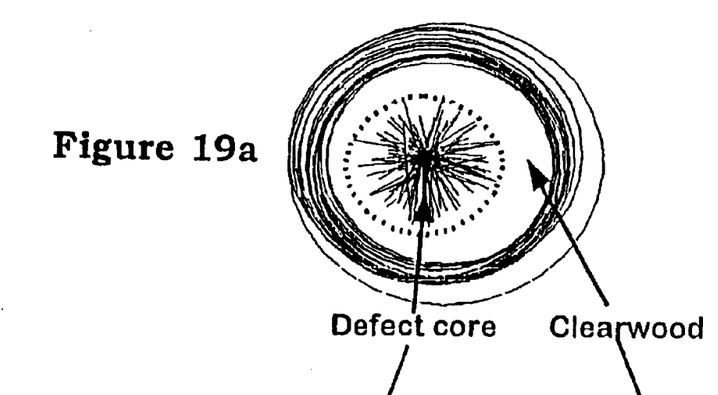
FIGS. 19a and 19b are a schematic the end view and longitudinal view of the log of FIGS. 13 to 18 showing the defect core and outer clearwood in the log.
Figure 19B:
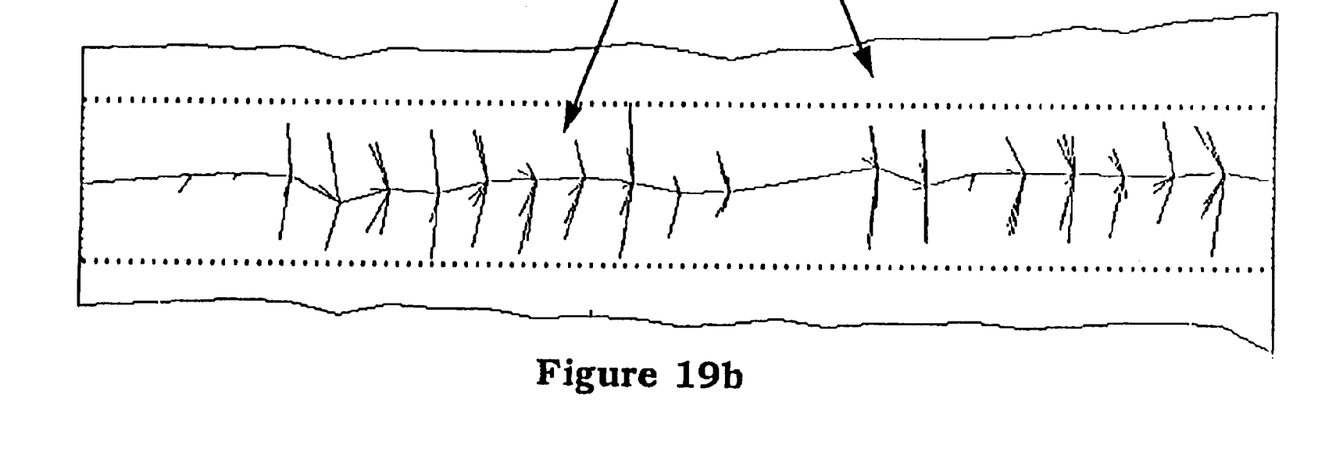

FIG. 19 shows the defect core zone and the outer clearwood zone in the log. The accurate determination of their location by radar imaging can be used by the AUTOSAW simulation software system to predict the range of wood products which may be cut from the log.

The system of the invention can also be effective identifying smaller structures within the stem or log and their position within the wood, such as annual growth rings, earlywood and latewood, sapwood/hardwood, resin pockets, internal checks, compression wood and possibly spiral grain.

The system of the invention could be used in conjunction with other non-destructive imaging techniques such as near infrared, mid infrared, ultraviolet and visible light, to improve both the precision and number of discrete characteristics which can be identified.

The foregoing describes the invention including preferred forms thereof. Alterations and modifications as will be obvious to those skilled in the art are intended to be incorporated within the scope hereof as defined in the appended claims.

What is claimed is:

1. A method for assessing standing tree stems, or for determining cutting points for processing of felled tree stems, logs, or wood pieces, or for assessing stems, logs, or wood pieces for end use, comprising scanning a stem, log or piece with shortwave or microwave electromagnetic energy, detecting the energy reflected from the wood, processing the resulting scan data to produce an image indicating hidden internal characteristics and their position within the stem, log, or piece, and assessing the image together with information as to the external shape or dimensions of the stem, log, or piece and identifying cutting points for the stem, log, or piece or allocating the stem, log, or piece or part of parts thereof to an end use.

2. A method according to claim 1 including obtaining information as to the external shape and dimensions of the stem, log, or piece and the depth of detected internal characteristics from the scan data.

3. A method according to claim 1 including scanning the stem, log, or piece, detecting the reflected energy, and processing the resulting scan data to produce an image indicating knots and/or whorls and their position, which are not visible from the exterior of the stem, log, or piece.

4. A method according to claim 3 also including producing an image indicating any one or more of a resin pocket, an internal check, one or more annual growth rings, one or more areas of early wood relative to late wood or vice versa and or more areas of sapwood relative to heartwood or vice versa, and the position of said internal characteristic(s).

5. A method according to claim 1 including determining the depth of the clearwood sheath from the surface of the stem, log, or piece.

6. A method according to claim 1 wherein the electromagnetic energy is radar frequency energy.

7. A method according to claim 1 wherein the electromagnetic energy is microwave frequency energy.

8. A method according to claim 1 wherein the electromagnetic energy has a frequency in the range of 0.5 to 20 GHz.

9. A method according to claim 1 wherein the electromagnetic energy has a frequency in the range of 5 to 10 GHz.

10. A method according to claim 1 wherein the electromagnetic energy has a frequency of about 8 GHz.

11. A method according to claim 1 including scanning the stem, log, or wood piece from more than one direction, detecting the energy reflected from the wood in each direction, and processing the scan data from each direction to produce the image of the stem, log, or wood piece.

12. A method according to claim 11 including carrying out said scanning in different directions via send and receive antennae positioned around the longitudinal axis of the stem, log, or wood piece.

13. A method according to claim 11 including carrying out said scanning in each direction simultaneously.

14. A method according to claim 1 wherein said scanning is carried out by moving a scanning device over the stem of a standing tree.

15. A method according to claim 1 wherein said scanning is carried out by moving a felled stem, or a log or wood piece on a conveyor past a scanning station including send and receive antennae.

16. A method as claimed in claim 1 including subsequently directing the stem, log, or wood piece to the production of solid wood or veneer or to pulp and paper production, based on assessment of said image of the stem, log, or wood piece.

17. Apparatus for assessing standing tree stems, or for determining cutting points for processing of felled tree stems, logs or other wood pieces, or for assessing stems, logs, or wood pieces for end use, comprising scanning means arranged to scan the stems, logs, or pieces with shortwave or microwave electromagnetic energy and to detect the energy reflected from the wood, associated computer processing means arranged to process the resulting scan data as to internal characteristics of the stem, log, or piece together with information as to the external shape or dimensions of the stem, log, or piece and produce an image of both the external shape and indicating hidden internal characteristics and their position, and the depth of clearwood, for each stem, log, or piece.

18. Apparatus according to claim 17 wherein said computer processing means is arranged to process the resulting scan data to obtain information as to the external shape and dimensions of the stem, log, or piece and the depth within the wood of detected internal characteristics from the scan data.

19. Apparatus according to claim 17 wherein the computer processing means is arranged to process the resulting scan data to produce an image indicating knots and/or whorls and their position, which are not visible from the exterior of the stem, log, or piece.

20. Apparatus according to claim 19 wherein the computer processing means is arranged to process the scan data to produce an image indicating any one or more of a resin pocket, an internal check, one or more annual growth rings, one or more areas of sapwood relative to heartwood or vice versa, one or more areas of early wood relative to late wood or vice versa, and the position of said internal characteristic(s).

21. Apparatus according to claim 17 wherein the computer processing means is arranged to determine the depth of the clearwood sheath from the surface of the stem, log, or wood piece.

22. Apparatus according to claim 17 wherein the electromagnetic energy is radar frequency energy.

23. Apparatus according to claim 17 wherein the electromagnetic energy is microwave frequency energy.

24. Apparatus according to claim 17 wherein the electromagnetic energy has a frequency in the range 0.5 to 20 GHz.

25. Apparatus according to claim 17 wherein the electromagnetic energy has a frequency in the rage of 5 to 10 GHz.

26. Apparatus according to claim 17 wherein the electromagnetic energy has a frequency of about 8 GHz.

27. Apparatus according to claim 17 wherein said scanning means is configured to scan the stems, logs, or wood pieces from more than one direction, detect the energy reflected from the wood in each direction, and the computer processing means is arranged to process the scan data from each direction to produce the image of each stem, log, or wood piece.

28. Apparatus according to claim 27 wherein the scanning means comprises send and receive antennae positioned around the longitudinal axis of the stem, log, or wood piece.

29. Apparatus according to claim 17 wherein said scanning means is adapted to be moved over the stem of a standing tree.

30. Apparatus according to claim 17 including associated computer processing means arranged to assess the images of each stem, log, or piece and allocate the stem, log, or piece to the production of solid wood or veneer or to pulp and paper production.

* * * * *